(12) United States Patent
Fago et al.

(10) Patent No.: US 8,269,201 B2
(45) Date of Patent: Sep. 18, 2012

(54) RADIOPHARMACEUTICAL PIG

(75) Inventors: Frank M. Fago, Mason, OH (US); Matt Bantly, Cincinnati, OH (US); David W. Wilson, Maineville, OH (US)

(73) Assignee: Mallinckrodt LLC, Hazelwood, MO (US)

( * ) Notice: Subject to any disclaimer, the term of this patent is extended or adjusted under 35 U.S.C. 154(b) by 1291 days.

(21) Appl. No.: 11/545,638

(22) Filed: Oct. 10, 2006

(65) Prior Publication Data

US 2007/0034537 A1  Feb. 15, 2007

Related U.S. Application Data

(63) Continuation of application No. 11/486,197, filed on Jul. 13, 2006, now Pat. No. 7,495,246, which is a continuation of application No. 10/527,301, filed as application No. PCT/US03/31823 on Oct. 7, 2003, now Pat. No. 7,165,672.

(60) Provisional application No. 60/419,161, filed on Oct. 17, 2002.

(51) Int. Cl.
G21F 5/015 (2006.01)
(52) U.S. Cl. ............... 250/506.1; 250/505.1; 250/507.1
(58) Field of Classification Search ............... 250/505.1, 250/506.1, 507.1
See application file for complete search history.

(56) References Cited

U.S. PATENT DOCUMENTS

| | | | |
|---|---|---|---|
| 1,931,798 A | 10/1933 | Hundt | |
| 2,682,352 A | 6/1954 | Hawkins et al. | |
| 2,812,231 A | 11/1957 | Zar | |
| 3,016,462 A | 1/1962 | Hendricksen et al. | |
| 3,074,542 A | 1/1963 | Myerson et al. | |
| 3,101,841 A | 8/1963 | Baldwin | |
| 3,149,717 A | 9/1964 | Castelli | |
| 3,272,322 A | 9/1966 | Ogle | |
| 3,294,231 A | 12/1966 | Vanderbeck | |
| D208,080 S | 7/1967 | Hamilton | |
| 3,329,146 A | 7/1967 | Waldman, Jr. | |
| 3,344,787 A | 10/1967 | Maclean | |
| 3,367,488 A | 2/1968 | Hamilton | |
| 3,531,644 A | 9/1970 | Kister | |

(Continued)

FOREIGN PATENT DOCUMENTS

EP       0 122 106       9/1960

(Continued)

OTHER PUBLICATIONS

Heller; "Radiation Safety in the Central Radiopharmacy"; Seminars in Nuclear Medicine; 1996; pp. 107-118; vol. 26, No. 2.

(Continued)

*Primary Examiner* — Michael Maskell
(74) *Attorney, Agent, or Firm* — Armstrong Teasdale LLP

(57) ABSTRACT

A pharmaceutical pig is used to transport a syringe containing a liquid radiopharmaceutical from a radiopharmacy to a medical facility for administration to a patient. The pharmaceutical pig includes an elongate polymer cap that is removably attached to an elongate polymer base. The elongate polymer cap includes a cap shell that completely encloses a cap shielding element and the elongate polymer base includes a base shell that completely encloses a base shielding element. Preferably the polymer utilized for the cap shell and the base shell is polycarbonate resin, e.g., LEXAN®. An inner liner is not utilized and the cap shielding element and the base shielding element, which are preferably, but not necessarily, made of lead, are completely sealed and unexposed.

41 Claims, 3 Drawing Sheets

U.S. PATENT DOCUMENTS

| | | | |
|---|---|---|---|
| 3,612,321 A | 10/1971 | Larson | |
| 3,618,836 A | 11/1971 | Bushnell | |
| 3,673,411 A | 6/1972 | Glasser | |
| 3,677,247 A | 7/1972 | Brown | |
| 3,732,423 A | 5/1973 | Peterson | |
| 3,770,964 A | 11/1973 | Backus | |
| 3,845,316 A | 10/1974 | Tureck | |
| 3,882,315 A | 5/1975 | Soldan | |
| 3,939,834 A | 2/1976 | McMahon | |
| 3,968,876 A | 7/1976 | Brookfield | |
| 3,971,955 A | 7/1976 | Heyer et al. | |
| 3,993,063 A | 11/1976 | Larrabee | |
| 4,060,073 A | 11/1977 | Collica et al. | |
| 4,062,353 A | 12/1977 | Foster et al. | |
| 4,074,824 A | 2/1978 | Kontes | |
| 4,081,688 A | 3/1978 | Fries | |
| 4,081,689 A | 3/1978 | Reiss | |
| 4,092,546 A | 5/1978 | Larrabee | |
| 4,106,622 A | 8/1978 | Windischman | |
| 4,113,090 A | 9/1978 | Carstens | |
| 4,122,836 A | 10/1978 | Burnett | |
| RE29,876 E | 1/1979 | Reese | |
| 4,200,804 A | 4/1980 | Farella et al. | |
| 4,208,588 A | 6/1980 | Rudin | |
| 4,246,709 A | 1/1981 | Selleslags | |
| 4,278,892 A | 7/1981 | Baatz et al. | |
| 4,282,441 A | 8/1981 | Filoramo | |
| 4,307,713 A | 12/1981 | Galkin et al. | |
| 4,357,541 A | 11/1982 | Ernst | |
| 4,393,864 A | 7/1983 | Galkin et al. | |
| 4,401,108 A | 8/1983 | Galkin et al. | |
| 4,447,729 A | 5/1984 | Doroszlai et al. | |
| 4,453,081 A | 6/1984 | Christ et al. | |
| 4,465,201 A | 8/1984 | Chalfant, Jr. | |
| 4,486,512 A | 12/1984 | Tozawa et al. | |
| 4,488,048 A | 12/1984 | Bienek et al. | |
| 4,494,666 A | 1/1985 | Cooper et al. | |
| 4,596,688 A | 6/1986 | Popp | |
| 4,626,380 A | 12/1986 | Baatz et al. | |
| 4,626,382 A | 12/1986 | Stritzke et al. | |
| 4,634,428 A | 1/1987 | Cuu | |
| 4,710,170 A | 12/1987 | Haber et al. | |
| 4,738,388 A | 4/1988 | Bienek et al. | |
| 4,743,233 A | 5/1988 | Schneider | |
| 4,750,092 A | 6/1988 | Werther | |
| 4,781,697 A | 11/1988 | Slaughter | |
| 4,846,235 A | 7/1989 | Handke | |
| 4,847,009 A | 7/1989 | Madle et al. | |
| 4,847,505 A | 7/1989 | Suthanthiran | |
| 4,851,702 A | 7/1989 | Perlman | |
| 4,869,299 A | 9/1989 | Handke | |
| 4,892,525 A | 1/1990 | Hermann, Jr. et al. | |
| 4,917,263 A | 4/1990 | Korb | |
| 4,923,088 A | 5/1990 | Tanaka et al. | |
| 4,979,616 A | 12/1990 | Clanton | |
| D313,470 S | 1/1991 | Talonn et al. | |
| 4,994,045 A | 2/1991 | Ranford | |
| 4,998,924 A | 3/1991 | Ranford | |
| 5,015,863 A | 5/1991 | Takeshima et al. | |
| 5,042,679 A | 8/1991 | Crowson et al. | |
| D324,101 S | 2/1992 | Reif et al. | |
| 5,096,062 A | 3/1992 | Burkardt et al. | |
| 5,099,998 A | 3/1992 | Curzon et al. | |
| 5,116,597 A | 5/1992 | Srivastava et al. | |
| 5,145,063 A | 9/1992 | Lee | |
| 5,157,900 A | 10/1992 | Kupersmit | |
| 5,163,916 A | 11/1992 | Sunderland | |
| D333,347 S | 2/1993 | Kemp et al. | |
| 5,197,602 A | 3/1993 | Biesecker et al. | |
| 5,205,408 A * | 4/1993 | Cobb | 206/364 |
| 5,205,824 A | 4/1993 | Mazur | |
| 5,235,795 A | 8/1993 | DeBusk | |
| 5,245,117 A | 9/1993 | Withers et al. | |
| 5,277,312 A | 1/1994 | Vumbaca | |
| D344,355 S | 2/1994 | Talonn et al. | |
| 5,293,993 A | 3/1994 | Yates, Jr. et al. | |
| 5,303,836 A | 4/1994 | Childress | |
| 5,308,329 A | 5/1994 | Mazur et al. | |
| 5,323,719 A | 6/1994 | Withers et al. | |
| 5,334,847 A | 8/1994 | Kronberg | |
| 5,348,544 A | 9/1994 | Sweeney et al. | |
| 5,385,105 A | 1/1995 | Withers, Jr. et al. | |
| 5,401,246 A | 3/1995 | Mazur et al. | |
| 5,403,287 A | 4/1995 | Talonn et al. | |
| 5,417,326 A | 5/1995 | Winer | |
| D364,501 S | 11/1995 | Gough | |
| 5,519,931 A * | 5/1996 | Reich | 29/426.3 |
| 5,529,189 A | 6/1996 | Feldschuh | |
| 5,536,945 A | 7/1996 | Reich | |
| 5,545,139 A | 8/1996 | Kriesel | |
| 5,552,612 A | 9/1996 | Katayama et al. | |
| 5,560,511 A | 10/1996 | McNerney | |
| 5,611,429 A | 3/1997 | Phillips | |
| 5,672,883 A | 9/1997 | Reich | |
| 5,716,317 A | 2/1998 | Okano et al. | |
| 5,775,019 A | 7/1998 | Johnson | |
| 5,782,804 A | 7/1998 | McMahon | |
| 5,789,648 A | 8/1998 | Roy et al. | |
| 5,828,073 A * | 10/1998 | Zhu et al. | 250/506.1 |
| 5,831,271 A * | 11/1998 | Okano et al. | 250/432 PD |
| 5,834,788 A | 11/1998 | Fu et al. | |
| D405,609 S | 2/1999 | Fu et al. | |
| 5,918,443 A * | 7/1999 | Phillips | 53/449 |
| 5,927,351 A | 7/1999 | Zhu et al. | |
| 6,047,488 A | 4/2000 | Tuszkiewicz | |
| RE36,693 E | 5/2000 | Reich | |
| D425,197 S | 5/2000 | Comer et al. | |
| 6,155,420 A | 12/2000 | Phillips | |
| 6,162,198 A | 12/2000 | Coffey et al. | |
| 6,199,699 B1 | 3/2001 | Eastman | |
| 6,243,936 B1 | 6/2001 | Biesecker et al. | |
| D447,231 S * | 8/2001 | Chen Fu et al. | D24/121 |
| 6,323,319 B1 | 11/2001 | White et al. | |
| 6,381,509 B1 | 4/2002 | Thiel et al. | |
| 6,405,729 B1 | 6/2002 | Thornton | |
| 6,425,174 B1 | 7/2002 | Reich | |
| 6,576,918 B1 * | 6/2003 | Fu et al. | 250/507.1 |
| 6,586,758 B2 | 7/2003 | Martin | |
| 6,722,499 B2 * | 4/2004 | Reich | 206/365 |
| 6,781,142 B2 | 8/2004 | Hutcheson | |
| 6,822,253 B1 * | 11/2004 | Martin et al. | 250/507.1 |
| 6,963,073 B2 * | 11/2005 | Martin et al. | 250/515.1 |
| 7,040,856 B2 * | 5/2006 | Reich | 414/810 |
| 7,086,133 B2 * | 8/2006 | Reich | 29/426.3 |
| 7,268,359 B2 * | 9/2007 | Fu et al. | 250/507.1 |
| 2001/0032851 A1 | 10/2001 | Pennington et al. | |
| 2002/0178566 A1 * | 12/2002 | Reich | 29/426.5 |
| 2002/0195575 A1 | 12/2002 | Martin | |
| 2003/0141210 A1 * | 7/2003 | Yanke et al. | 206/364 |
| 2003/0222228 A1 * | 12/2003 | Chen Fu et al. | 250/507.1 |
| 2004/0016098 A1 | 1/2004 | Reich | |
| 2005/0198800 A1 * | 9/2005 | Reich | 29/426.3 |
| 2005/0234424 A1 | 10/2005 | Besign et al. | |

FOREIGN PATENT DOCUMENTS

| | | |
|---|---|---|
| EP | 0 739 017 | 10/1962 |
| EP | 0286992 A2 | 10/1988 |
| EP | 0344966 A1 | 12/1989 |
| EP | 0344966 B1 | 12/1989 |
| EP | 0350186 B1 | 1/1990 |
| FR | 1 518 130 | 3/1968 |
| FR | 2308382 | 11/1976 |
| FR | 2 801 414 | 5/2001 |
| GB | 1269290 | 4/1972 |
| GB | 1572650 | 7/1980 |
| GB | 849 655 | 10/1984 |
| GB | 2198682 A | 6/1988 |
| GB | 908 134 | 10/1996 |
| JP | 2095380 | 4/1990 |
| JP | 404315098 A | 11/1992 |
| JP | 7231925 | 9/1995 |
| JP | 8098869 | 4/1996 |
| JP | 199698869 | 4/1996 |
| JP | 8238297 | 9/1996 |
| JP | 10104389 | 4/1998 |
| JP | 11114062 | 4/1999 |
| JP | 11164886 | 6/1999 |

| JP | 11169430 | 6/1999 |
| JP | 2000167053 | 6/2000 |
| JP | 01349984 | 12/2001 |
| WO | 9525331 | 11/1994 |
| WO | 0052707 | 9/2000 |
| WO | 0070624 | 11/2000 |
| WO | 0122430 A1 | 3/2001 |

OTHER PUBLICATIONS

Leonard et al.; "Syringe Radiation Shield for Short-Lived Radionuclides"; Australasian Radiology; Aug. 1971; pp. 299-301;vol. 15, No. 3; Australia.

Miyazaki et al.; "Reduction of Radiation Doses to the Worker in Preparing the Radiopharmaceutical Solution by a Simple Shielding Equipment"; Radioisotopes; Jan. 1987; pp. 32-35; vol. 36, No. 1.

Montgomery et al; "Reductions in finger doses for radiopharmaceutical dispensing afforded by a syringe shield and an automatic dose dispenser"; Nuclear Medicine Communications; 1999; pp. 189-194; vol. 20.

Picket et al; "The Incidence of Blood Contamination of Lead Unit Dose Containers With and Without Single-Use Protective Inserts Used with Commercially Prepared Radiopharmaceutical Unit Doses"; Journal of Nuclear Medicine Technology; 1998; pp. 200-203; vol. 26, No. 3.

Hilditch et al.; "Fifteen years of Radiological Protection Experience in a Regional Radiopharmacy"; Health Physics; 1990; pp. 109-116; vol. 59, No. 1.

Hastings et al; "An assessment of finger doses received by staff while preparing and injecting radiopharmaceuticals"; Nuclear Medicine Communications; 1997; pp. 785-790; vol. 18.

Green et al; "Comparison of Exposure Rates from various Iodine 131 NaI Therapeutic Capsule Lead Shields: Improved Designs Utilizing Tungsten"; Journal of the American Pharmaceutical Association; 2001; vol. 41, No. 2.

Abstract from the Proceedings of the 44th Annual Meeting of the Society of Nuclear Medicine; Jun. 1-4, 1997; p. 146; San Antonio Texas Posterboard 1500.

Research confirms validity of Syncor's Secure Safety System; Syncor International Corp. Business Wire; Jun. 2, 1997; p. 1.

"New Dose Calibrator Shielded Work Platform Brings a Higher Level of Radiation Safety to Nuclear Medicine"; Product News, Clinical Nuclear Medicine; 1996; pp. 179-180; vol. 21.

"We keep our pigs clean"; Advertisement, Syncor Pharmacy Services; Journal of Nuclear Medicine Technology; 1997; vol. 25, No. 3.

"Biodex Medical Systems Shielding Specialists"; Advertisement, Biodex Medical Systems, Inc.; Journal of Nuclear Medicine Technology; 1997; vol. 25, No. 1.

Miles; "Bloodborne Pathogens Standard applicability to radiopharmaceutical use"; www.osha.gov, U.S. Dept. of Labor; May 18, 1998; pp. 1-2.

ENB Region 8 Completed Applications Jun. 20, 2001; www.dec.ny.gov; 2001; pp. 1-2.

Syncor Products, Nuclear Medicine Catalog, "Nuclear Medicine Services, Supplies, and Heath Physics Associates" pp. 1, 25 and 132 (2003) http://www.syncor.com/products/catalog.asp.

* cited by examiner

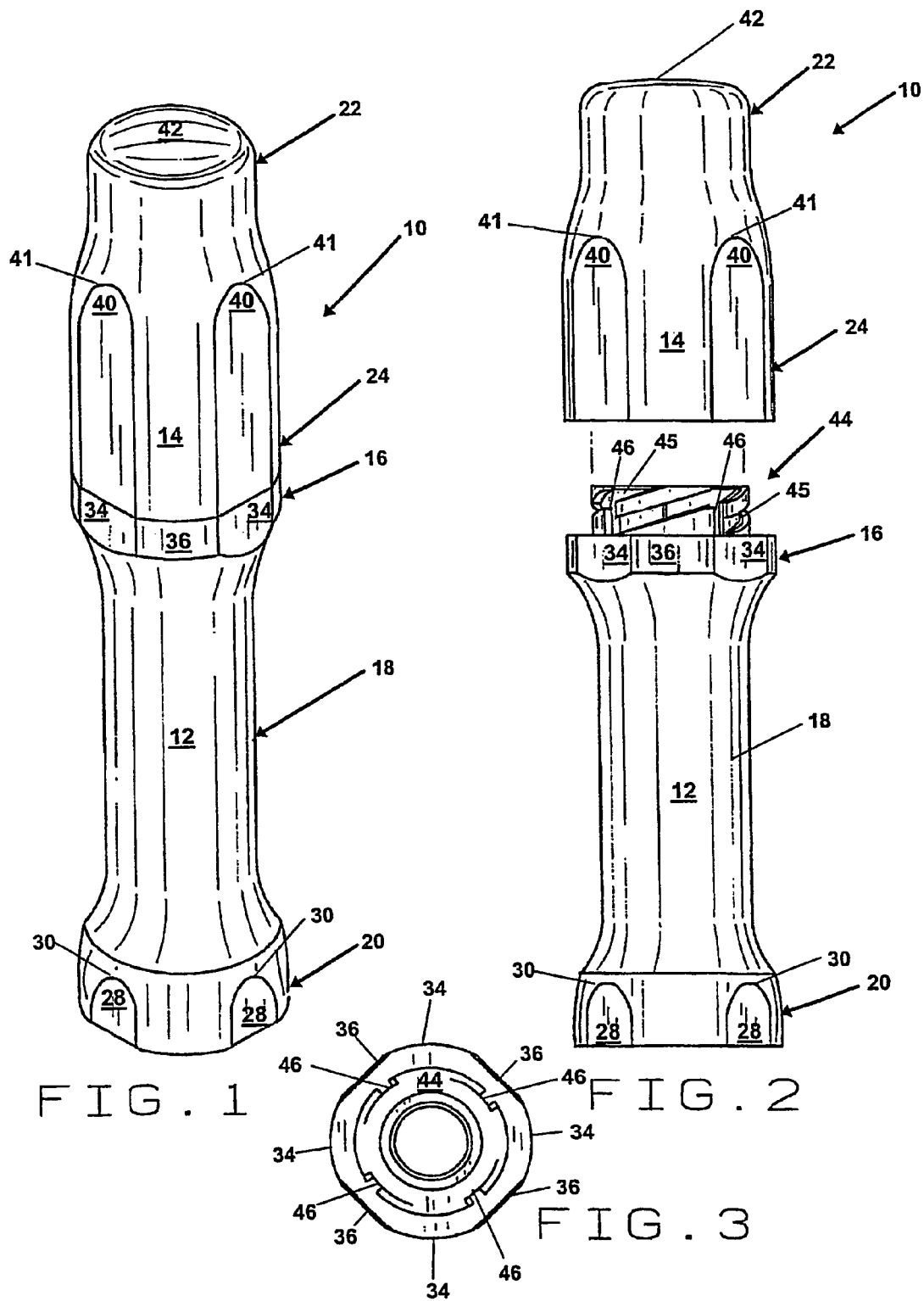

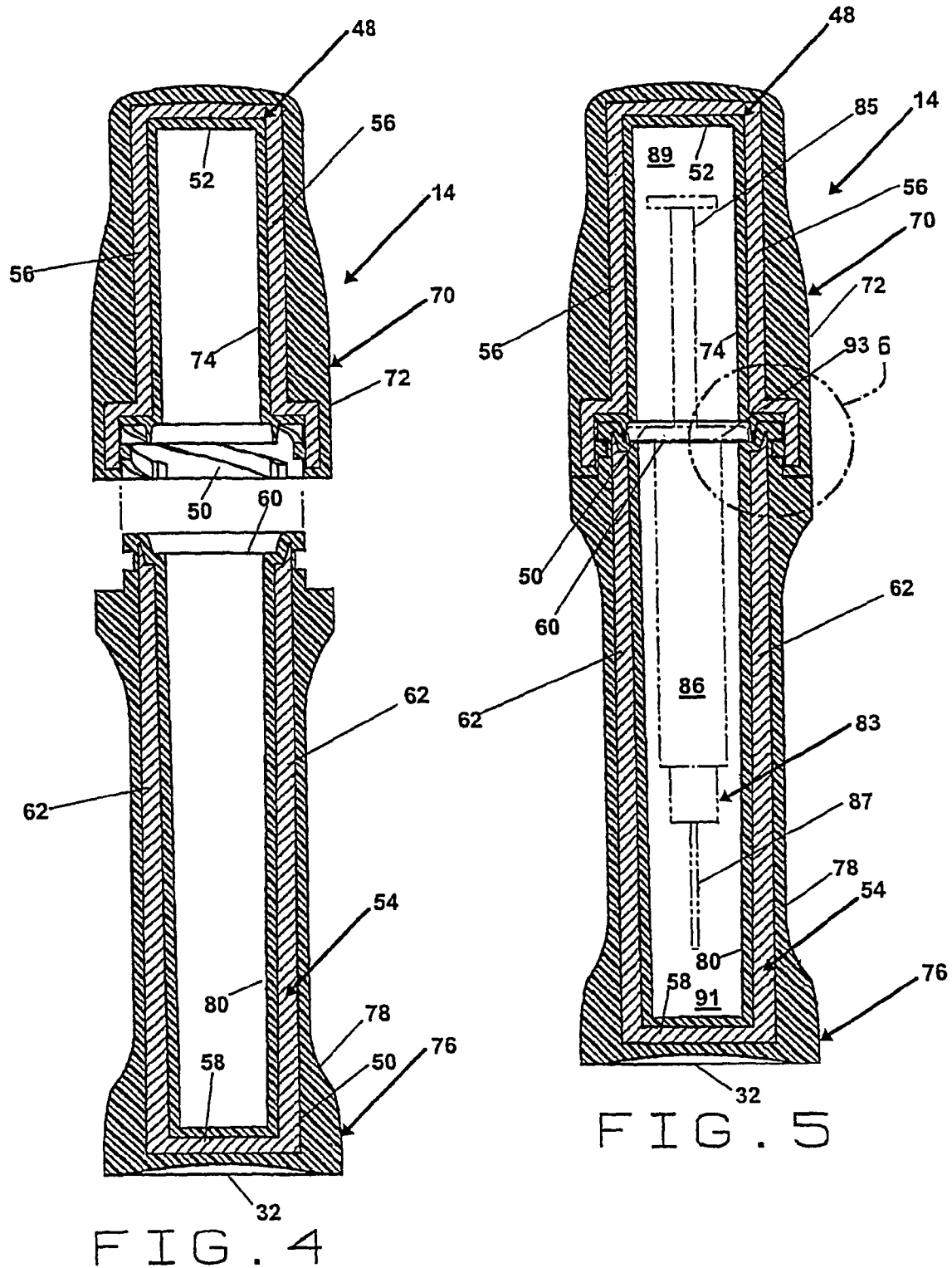

RADIOPHARMACEUTICAL PIG

CROSS-REFERENCE TO RELATED APPLICATIONS

This application is a continuation of U.S. patent application Ser. No. 11/486,197 entitled "Radiopharmaceutical Pig" filed on 13 Jul. 2006, now U.S. Pat. No. 7,459,246 which is a continuation of U.S. patent application Ser. No. 10/527,301 entitled "Polymer Pharmaceutical Pig and Associated Method of Use and Associated Method of Production" filed on 9 Mar. 2005, now U.S. Pat No. 7,165,672 which claims priority to PCT Application No. PCT/US03/31823 filed on 7 Oct. 2003, which claims priority to U.S. Provisional Patent Application No. 60/419,161 filed on 17 Oct. 2002, the entire disclosures of which are hereby incorporated by reference in their entireties.

BACKGROUND OF INVENTION

A pharmaceutical pig is used for transportation of liquid radiopharmaceuticals. A radiopharmacy typically dispenses a liquid radiopharmaceutical into a syringe, which is then placed in a pharmaceutical pig for transport to a medical facility. The pharmaceutical pig reduces unwanted exposure from the radioactive material and protects the syringe from damage. After delivery, the pharmaceutical pig is opened, the syringe is removed and the radiopharmaceutical is administered to a patient. The used syringe is put back in the pharmaceutical pig and returned to the radiopharmacy for disposal. Some radiopharmacies are independently owned and others are owned and operated in nationwide networks by Cardinal Health, Inc., having a place of business at 7000 Cardinal Place, Dublin, Ohio 43017 and Mallinckrodt Inc., a business of Tyco International, Ltd. Conventional pharmaceutical pigs are used on a daily basis by radiopharmacies across the country. Many of the conventional pigs in current use are formed from plastic and lead. Of course, the lead is used as shielding material for the radiopharmaceutical. Conventional plastic/lead pharmaceutical pigs are typically configured in a two-part or a three-part design, discussed in greater detail below. Other conventional pharmaceutical pigs are formed from plastic and tungsten. The tungsten is an alternative shielding material to lead, but it is much more expensive.

The pharmaceutical pigs that are currently used with syringes are elongate devices sized to enclose a single syringe that holds a dose for a single patient. Conventional two-part pharmaceutical pigs are available from Biodex Medical Systems, Inc. of Shirley, N.Y. ("Biodex") and are commonly used in the Mallinckrodt system of radiopharmacies. Conventional three-part pharmaceutical pigs are produced by Cardinal Health, Inc. and are shown in U.S. Pat. No. 5,519,931. These conventional three-part pharmaceutical pigs are believed to be in widespread use in the Cardinal Health, Inc. system of radiopharmacies to transport conventional syringes.

The Biodex two-part pharmaceutical pig is formed from: a) an outer plastic shell having a removable plastic top that threadibly engages a plastic base; and b) an inner shield having an upper lead section that fits in the plastic top and a lower lead section that fits in the plastic base. Conventional syringes are transported in this two-part pharmaceutical pig. However, because of the possibility of contamination, the lower section of the pharmaceutical pig is washed and disinfected after each use in the Mallinckrodt system of radiopharmacies.

There is a three-part pharmaceutical pig disclosed in U.S. Pat. No. 5,519,931, assigned to Syncor International Corp., which is formed from the following components: a) an outer shell having a removable plastic top that threadibly engages a plastic base; b) an inner shield having an upper lead section that fits in the plastic top and a lower lead section that fits in the plastic base; and c) an inner disposable liner having a removable plastic cap that connects to a plastic base. A conventional syringe is contained in the disposable plastic liner, which fits into the lead portion of the pharmaceutical pig. There is also a pharmaceutical pig disclosed in U.S. Pat. No. 6,425,174, which is also assigned to Syncor International Corp., that includes an upper shield and a lower shield that nest within an upper outer shell and a lower outer shell, respectively. There is a separate sharps container, having an upper cap and a lower housing, that nests within the upper shield and the lower shield, respectively.

John B. Phillips is listed as the inventor on several patents for a three-part pharmaceutical pig having: a) an outer plastic shell; b) an inner lead shield; and c) a removable inner liner to hold a syringe. The Phillips' patents are as follows: U.S. Pat. Nos. 5,611,429; 5,918,443; and 6,155,420. The removable inner liner in the Phillips' design has a flared hexagonal shaped section sized to surround the finger grip of the syringe and hold it securely in place during transit.

Conventional three-part lead/plastic pharmaceutical pigs, such as the Syncor design or the Phillips design described above, rely on a removable inner liner having a cap and base to contain the syringe and prevent contamination of the lead shielding material with the radiopharmaceutical. However, both the two-part lead/plastic pharmaceutical pig and the three-part lead/plastic pharmaceutical pig have exposed lead on the interior. There is a need for a new design that protects the lead from inadvertent contamination by the liquid radiopharmaceutical. Lead is a very porous material that can absorb the radiopharmaceutical. Moreover, lead, as a material, might be construed as being hygienically challenging.

Many conventional three-part lead/plastic pharmaceutical pigs use a threaded design to connect the cap and the base. Some of these prior art designs require several turns to connect the cap and the base. In a busy radiopharmacy, there is a need for a faster and easier way to attach the cap to the base. However, the cap is typically not locked into place, therefore, rough transportation and a failure to provide the requisite number of turns can result in the cap untwisting slightly from the base during transit with a potential spill of radioactive pharmaceutical fluid resulting therefrom. Another issue is that the base of a conventional pharmaceutical pig is generally cylindrical making the pharmaceutical pig prone to tipping and falling over on its side. The present invention is directed to overcoming one or more of the problems set forth above. These deficiencies and shortcomings include, but are not limited to, exposed lead, numerous turns required to attach the cap to the base, absence of a locking mechanism to secure the cap to the base and a cylindrical base where the bottom portion of the base has substantially the same diameter as the top portion of the base so that the pharmaceutical pig is prone to tipping and falling over on its side.

SUMMARY OF INVENTION

A pharmaceutical pig is sized and arranged to transport a single syringe containing a unit dose of a radiopharmaceutical from a radiopharmacy to a medical facility such as a doctor's office, clinic or hospital. After the radiopharmaceutical has been administered to a patient, the used syringe is put back into the pharmaceutical pig and returned to the radiopharmacy for proper disposal. The present invention may be used with conventional syringes or safety syringes.

In one aspect of this present invention, a polymer pharmaceutical pig is disclosed. The polymer pharmaceutical pig includes an elongate polymer base having a base shell that completely encloses a base shielding element and having a first hollow center section and an elongate polymer cap that is removably attached to the elongate polymer base, the elongate polymer cap, having a second hollow center and a cap shell that completely encloses a cap shielding element.

Moreover, for convenience and ease of use, the amount of rotation of the elongate polymer cap in relation to the elongate polymer base for removably attaching the elongate polymer base to the elongate polymer cap is minimized, i.e., preferably less than three hundred and sixty degrees (360°), more preferably less than one hundred and eighty degrees (180°) and optimally less than ninety degrees (90°). Preferably, a locking detent is located in the threaded interconnections to secure the elongate polymer base to the elongate polymer cap. The polymer material utilized in the base shell and the cap shell can include virtually any type of plastic and is preferably polycarbonate resin, e.g., LEXAN® material, while the base shielding element and the cap shielding element can be made of virtually any type of material that blocks radiation emitted from the radiopharmaceutical. This material preferably includes lead as well as tungsten and metallic-filled polymers, with lead being the most preferred material due to the low cost and ease of manufacturing.

Preferably, the elongate polymer cap is substantially cylindrical and the bottom portion of the elongate polymer base is substantially bell-shaped. Moreover, the elongate polymer base of the pharmaceutical pig preferably includes a top portion having a first diameter, a middle portion having a second diameter and a bottom portion having a third diameter, where the second diameter of the middle portion is less than the first diameter of the top portion and is less than the third diameter of the bottom portion. The elongate polymer cap of the pharmaceutical pig preferably includes a top portion having a fourth diameter and a bottom portion having a fifth diameter, where the fourth diameter of the top portion is less than the fifth diameter of the bottom portion.

In the preferred design, the top portion of the elongate base includes a plurality of flattened portions, where at least one flattened portion of the plurality of flattened portions includes an arch-like portion and the bottom portion of the elongate base includes a plurality of flattened portions, wherein at least one flattened portion of the plurality of flattened portions includes an arch-like portion. The bottom portion of the elongate cap base includes a plurality of flattened portions, where at least one flattened portion of the plurality of flattened portions includes an arch-like portion. Optimally, at least one flattened portion of the plurality of flattened portions in the top portion of the elongate base is substantially aligned with the at least one flattened portion of the plurality of flattened portions in the bottom portion of the elongate cap.

In another aspect of this present invention, an assembly including a pharmaceutical pig sized and arranged to transport a syringe is disclosed. The assembly includes a syringe having a needle, a barrel, a pair of wing-shaped finger grips, and a plunger, and a pharmaceutical pig including an elongate polymer base that completely encloses a base shielding element. The elongate polymer base having a first hollow center section that is sized to surround the needle and at least a portion of the barrel of the syringe and an elongate polymer cap that is removably attached to the elongate polymer base. The elongate polymer cap completely encloses a cap shielding element and the elongate polymer cap includes a second hollow center section that is sized to surround at least a portion of the plunger of the syringe.

In still another aspect of this present invention, a method for transporting a syringe in a pharmaceutical pig, the syringe having at least a needle, a barrel, a pair of wing-shaped finger grips, and a plunger is disclosed. The method includes placing a syringe containing a liquid radiopharmaceutical in a pharmaceutical pig having an elongate polymer base that completely encloses a base shielding element. The elongate polymer base having a first hollow center section that is sized to surround the needle and at least a portion of the barrel of the syringe and an elongate polymer cap that is removably attached to the elongate polymer base. The elongate polymer cap completely encloses a cap shielding element and the elongate polymer cap having a second hollow center section that is sized to surround at least a portion of the plunger of the syringe. This is followed by transporting the pharmaceutical pig containing the syringe to a medical facility and then transporting the pharmaceutical pig and the used syringe back to the radiopharmacy for disposal of the used syringe.

In yet another aspect of this present invention, a method for producing a pharmaceutical pig is disclosed. The method includes molding a base shielding element in a first mold, molding a cap shielding element in a second mold. This is followed by inserting the base shielding element within a third mold and injecting molten polymer material into the third mold so that when the polymer material hardens, the base shielding element is completely enclosed by the polymer material to form an elongate base. This is then followed by inserting the cap shielding element within a fourth mold and injecting molten polymer material into the fourth mold so that when the polymer material hardens, the cap shielding element is completely enclosed by the polymer material to form an elongate cap.

These are merely some of the innumerable illustrative aspects of this present invention and should not be deemed an all-inclusive listing. These and other aspects will become apparent to those skilled in the art in light of the following disclosure and accompanying drawings.

BRIEF DESCRIPTION OF DRAWINGS

For a better understanding of the present invention, reference may be made to the accompanying drawings in which:

FIG. 1 is a perspective view of an embodiment of the assembled pharmaceutical pig of the present invention;

FIG. 2 is a side elevation view of the pharmaceutical pig of the present invention with an elongate cap separated from an elongate base;

FIG. 3 is a top view of the elongate base for the pharmaceutical pig of the present invention without an elongate cap;

FIG. 4 is a section view of the pharmaceutical pig of the present invention with an elongate cap, having a cap shield enclosed by a cap shell, and the elongate base, having a base shield enclosed by a base shell, with the elongate cap separated from the elongate base;

FIG. 5 is a section view of the assembled pharmaceutical pig of the present invention with an elongate cap, having a cap shield enclosed by a cap shell, and the elongate base, having a base shield enclosed by a base shell, and with a syringe positioned inside the pharmaceutical pig.

DETAILED DESCRIPTION

Figure 6:
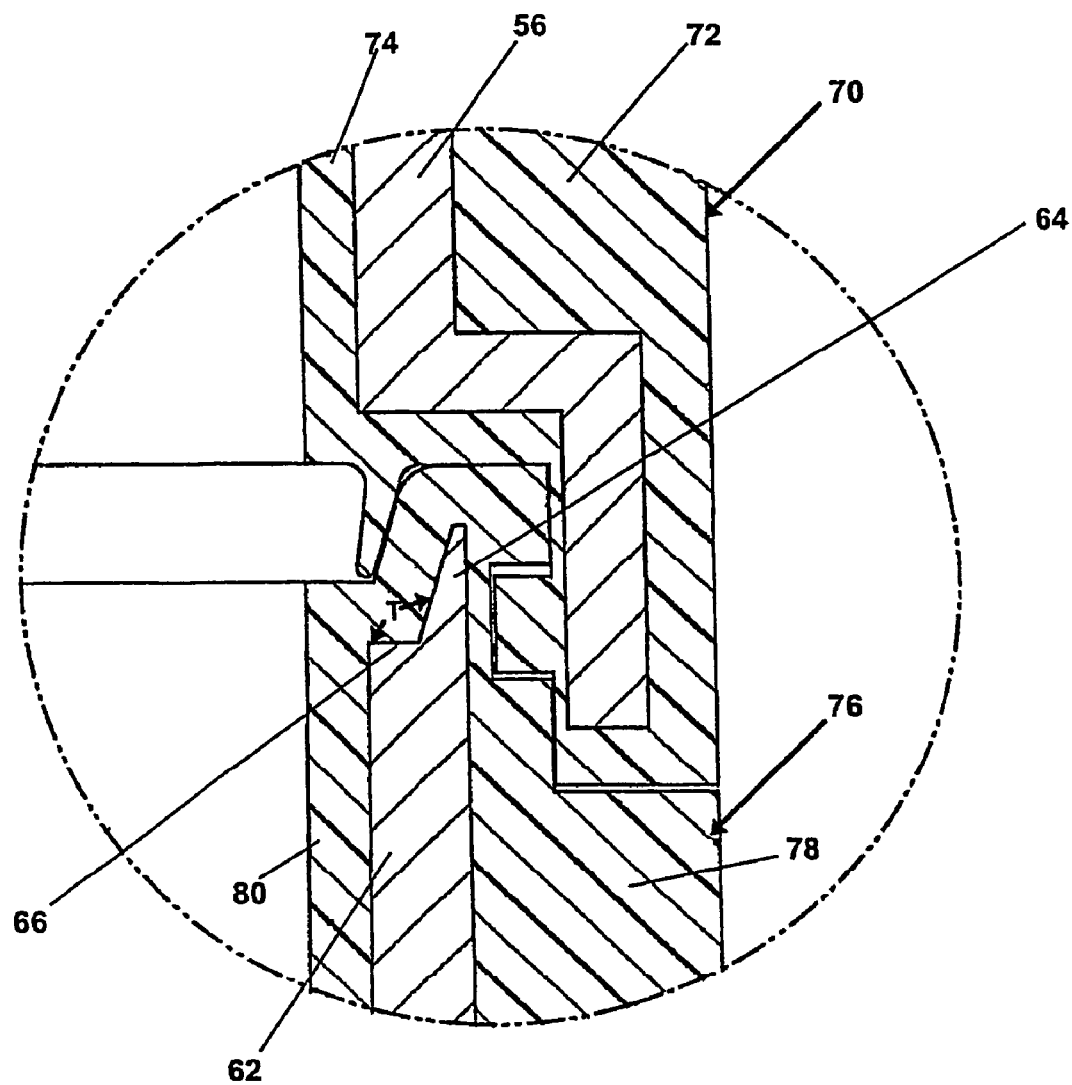
FIG. 6 is an isolated, close-up view of the threaded joint between the elongate cap and the elongate base, as shown in FIG. 5, when the pharmaceutical pig of the present invention is fully assembled and a syringe is positioned within the pharmaceutical pig.

FIG. 1 is a perspective view of the embodiment of the pharmaceutical pig of the present invention that is generally indicated by numeral 10. There is an elongate base 12 and an elongate cap 14. The elongate base 12 and the elongate cap 14 of the pharmaceutical pig 10 can be formed in any of a wide variety of shapes and sizes, however, a substantially cylindrical shape is preferred. Preferably, the elongate base 12 includes a top portion that is generally indicated by numeral 16 having a first diameter, a middle portion that is generally indicated by numeral 18 having a second diameter and a bottom portion that is generally indicated by numeral 20 having a third diameter. The elongate cap 14 includes a top portion that is generally indicated by numeral 22 having a fourth diameter and a bottom portion that is generally indicated by numeral 24 having a fifth diameter. In the preferred embodiment, the second diameter of the middle portion 18 of the elongate base 12 is less than the first diameter of the top portion 18 of the elongate base 12. The second diameter of the middle portion 18 of the elongate base 12 is also less than the third diameter of the bottom portion 20 of the elongate base 12 to create a bell-shape. Also, in the preferred embodiment, the fourth diameter of the top portion 22 of the elongate cap 14 is less than the fifth diameter of the bottom portion 24 of the elongate cap 14.

The elongate base 12 for the pharmaceutical pig 10, preferably includes a first plurality of flattened portions 28, e.g., four (4), that each include an arch-like portion 30 located on the bottom portion 20 of the elongate base 12 of the pharmaceutical pig 10. The bottom portion 20 of the elongate base 12 is preferably bell-shaped to prevent tipping and includes a domed, bottom surface 32 to reduce material cost, as shown in FIGS. 4 and 5.

Referring again to FIGS. 1 and 2, the top portion 16 of the elongate base 12 for the pharmaceutical pig 10, preferably and optionally, includes a second plurality of flattened portions, e.g., four (4), that preferably alternate between rectangular portions 36 and rectangular portions that each have a downwardly extending arch-like portion 34.

The elongate cap 14 for the pharmaceutical pig 10, preferably and optionally, includes a third plurality of flattened portions 40, e.g., four (4), that each include an arch-like portion 41. The top portion 22 is preferably circular and includes a flat top surface 42, as shown in FIG. 1, which can be labeled as well as easily transported within a delivery case that can hold a multiple number of pharmaceutical pigs 10.

There is a plurality of threaded interconnections, which is generally indicated by numeral 44, as shown in FIG. 2. Preferably, but not necessarily, there are four (4) threads 45. Preferably, with the present pharmaceutical pig 10 of the present invention, the amount of turns required to secure the elongate base 12 to the elongate cap 14 is minimized. The preferred amount of turning being one turn (360°) or less, with a more preferred amount of turning being one-half of a turn (180°) or less and the most preferred amount of turning being one-quarter of a turn (90°) or less. The pitch of the threads 45 can vary greatly depending on the parameters of the pharmaceutical pig 10, with the most preferred value of pitch being 1.38 for the threads 45.

Referring now to FIG. 3, there is a series of locking detents 46 that secure the elongate base 12 to the elongate cap 14. These locking detents 46 lock the elongate base 12 to the elongate cap 14 when the threads 45 of the elongate cap 14 and the elongate base 12 are completely engaged. The elongate cap 14 is flush against the elongate base 12 after having completed the maximum amount of turning, e.g., one-quarter of a turn (90°) to seal the elongate cap 14 against the elongate base 12 in fluid-tight relationship. This seal is present without the presence of an additional component that requires replacement and maintenance, such as an o-ring.

Located within the elongate cap 14 and elongate base 12 is a cap shielding element that is generally indicated by numeral 48 and the base shielding element that is generally indicated by numeral 54, respectively, as shown in FIGS. 4 and 5. These shielding elements 48 and 54 are typically formed from lead because it is relatively inexpensive and easy to form. Moreover, these shielding elements 48 and 54 can be formed from any material that blocks the radiation that is emitted from the radiopharmaceutical. For example, tungsten is a suitable shielding element, but it is more expensive than lead and more difficult to form or mold. Metallic-filled polymer composite materials such as the ECOMASS® compounds produced by Engineered Materials, a M. A. Hanna Company having a place of business in Norcross, Ga. can also be used as shielding material.

The cap shielding element 48 has a closed end 52 and an open end 50. The walls 56 of the cap shielding element 48 are of generally uniform thickness. The base shielding element 54 has a closed end 58 and an open end 60. The walls 62 of the base shielding element 54 are of generally uniform thickness.

As shown in FIG. 5 and best illustrated in FIG. 6, the walls 62 of the base shielding element 54 form a protrusion 64, which is preferably but not necessarily triangular, which forms an angle T when measured against the inside wall of the base shielding element 54. The base shielding element 54 includes a ledge near the open end 60 that forms a shoulder 66.

Referring again to FIGS. 4 and 5, the cap shielding element 48 of the elongate cap 14 is completely enclosed by a cap shell 70 having an outer cap shell portion 72 and an inner cap shell portion 74. Also, the base shielding element 54 of the elongate base 12 is completely enclosed by a base shell 76 having an outer base shell portion 78 and an inner base shell portion 80.

The cap shell 70 and base shell 76 are preferably made of polymer material. This can include virtually any type of plastic, however, the most preferred type of material is a polycarbonate resin. A specific type of polycarbonate resin, which can be utilized with the present invention, can be purchased under the mark LEXAN®, which is a federally registered trademark of the General Electric Company, having a place of business at One Plastics Avenue, Pittsfield, Mass. 01201. LEXAN® is very lightweight, but is also known for its impact resistance, clarity, stability and heat resistance.

The preferred method of forming the cap shell 70 and base shell 76 so that the cap shell 70 and base shell 76 enclose and seal the cap shielding element 48 of the elongate cap 14 and the base shielding element 54 of the elongate base 12, respectively, is by the process of molding. Although the polymer material can be molded in two parts and then melted or welded to provided the complete enclosure of the cap shielding element 48 of the elongate cap 14 and the base shielding element 54 of the elongate base 12, the preferred method of molding the polymer material is by a "two-shot" or "overmolding" process.

Examples of this "two-shot" or "overmolding" process are described in: U.S. Pat. No. 4,750,092, which issued to Werther on Jun. 7, 1988 and was assigned to Kollmorgen Technologies Corporation, which is incorporated herein by reference; U.S. Pat. No. 6,381,509, which issued to Thiel et al. on Apr. 30, 2002; and was assigned to Mattec, Inc, which is incorporated herein by reference; and U.S. Pat. No. 6,405,729, which issued to Thornton on Jun. 18, 2002, which is incorporated herein by reference.

A significant advantage of the present invention is that no inner liner is utilized. This is a significant advantage since inner liners are typically discarded after each use. This reduces cost and eliminates waste.

As also shown in FIG. 5, there is a syringe 83, having: a needle 87 shown in phantom; a barrel 86; a plunger 85; and finger grips 93 which are sometimes called wings. The finger grips 93 may be hexagonal, circular or polygonal; they may fully or partially surround the barrel 86. The finger grips 93 are captured between the previously described shoulder portion 66 formed in the inner base shell portion 80 of the base shell 76 and the inner cap shell portion 74 of the cap shell 70. The syringe 83 is therefore prevented from lateral movement inside the pharmaceutical pig 10 during transit. The needle 87 and at least a portion of the barrel 86 are positioned in a first hollow center section 91 of the elongate base 12. At least a portion of the plunger 85 is positioned in a second hollow center section 89 of the elongate cap 14.

The pharmaceutical pig 10 is believed to comply with the revised Bloodborne Pathogens Standard (29 C.F.R. Sectional 1910.1030(d)(2)) promulgated by the Occupational Safety and Health Administration by fully meeting their definition of a "sharps container" by providing a container that is: puncture resistant; capable of being labeled or color-coded; leakproof on the sides and bottom; and does not require a healthcare provider to reach by hand into the container where the sharp has been placed.

Method of Use for the Pharmaceutical Pig 10:

A prescription is called in, faxed in, or otherwise given to a radiopharmacy. The pharmacist enters the prescription in a computer and prints out the labels. A self-adhesive label can be attached to the pharmaceutical pig 10 in a conventional fashion. In the alternative, a label can be attached to the pharmaceutical pig with the flexible sleeve (not shown), without the need for adhesives. A separate label is affixed to a safety syringe or a conventional syringe. The syringe 83 is filled with a radiopharmaceutical in accordance with the prescription. The filled syringe 83 is assayed. In other words, the activity of the radiopharmaceutical in the syringe 83 is measured in a dose calibrator to verify that it complies with the prescription. The filled syringe 83 is put in the pharmaceutical pig 10 and then closed. The pharmaceutical pig 10 is wipe tested for contamination. If the pharmaceutical pig 10 passes the wipe test, it is placed in a delivery container.

The delivery containers used by some Mallinckrodt Inc. pharmacies have interior padding of rubber foam. Several pharmaceutical pigs 10 may be placed in a single delivery container. Before leaving the radiopharmacy, the delivery container and the pharmaceutical pigs 10 are wipe tested and surveyed. If the delivery container passes, a DOT label is affixed to the outside of the delivery container and it is delivered to a medical facility.

The pharmaceutical pigs 10 are then opened and the syringe 83 is placed in an injection shield. The radiopharmaceutical is administered to the patient. The delivery case with the pharmaceutical pigs 10 and used syringes 83 are then returned to the radiopharmacy. The syringe 83 is removed from the pharmaceutical pig 10 and placed in a disposal bin. The pharmaceutical pig 10 is then washed and dried. The pharmaceutical pig 10 is then ready to be reused.

Method of Producing the Pharmaceutical Pig 10:

This involves first molding the base shielding element 54 by pouring molten, nuclear shielding, material into a first mold (not shown). The preferred substance is lead, as opposed to tungsten or metallic-filled polymers, due to cost considerations and ease of molding. When the base shielding element 54 has solidified, the base shielding element 54 is then placed into an injection molding machine (not shown). The polymer material, e.g., polycarbonate resin, is then injected and flows into a third mold, having a mold cavity, which surrounds the base shielding element 54. After an application of temperature and pressure, a solidified elongate base 12 is released from the mold. This elongate base 12 includes the base shielding element 54, which is now completely enclosed by a base shell 76. The base shell 76 includes an inner base shell portion 80 that is adjacent to the needle 87 and barrel 86 of the syringe 83 and an outer base shell portion 78 that forms the outer surface of the elongate base 12. In the same manner, the cap shielding element 48 is created by pouring molten, nuclear shielding, material into a second mold (not shown). As with the base shielding element 54, the preferred substance is again lead. When the cap shielding element 48 has solidified, the cap shielding element 48 is placed into an injection molding machine (not shown). The polymer material, e.g., polycarbonate resin, is then injected and flows into a fourth mold, having a mold cavity, which surrounds the cap shielding element 48. After an application of temperature and pressure, a solidified elongate cap 14 is released from the mold. This elongate cap 14 includes the cap shielding element 48, which is now completely enclosed by the cap shell 70. The cap shell 70 includes an inner cap shell portion 74 that is adjacent to the plunger 85 of the syringe 83 and an outer cap shell portion 72 that forms the outer surface of the elongate cap 14.

Although a preferred embodiment of the pharmaceutical pig 10, a method of use of the pharmaceutical pig 10 and a method of production for the pharmaceutical pig 10 have been illustrated in the accompanying Drawings and described in the foregoing Detailed Description, it is understood that the invention is not limited to the embodiment disclosed, but is capable of numerous rearrangements, modifications and substitutions without departing from the spirit for the invention as set forth and defined by the following claims.

The invention claimed is:

1. A radiopharmaceutical pig comprising:
   an elongate base comprising:
      a radiation-blocking base shielding element having an open end, a closed end, and at least one wall extending between the open and closed ends, wherein the closed end and the at least one wall define an interior of the base shielding element, and wherein the base shielding element comprises lead; and
      a polymeric base shell that completely encloses an entirety of the base shielding element, the base shell defining a hollow section of the base;
   a cap comprising:
      a radiation-blocking cap shielding element having an open end, a closed end, and at least one wall extending between the open and closed ends, wherein the closed end and the at least one wall define an interior of the cap shielding element, and wherein the cap shielding element comprises lead; and
      a polymeric cap shell that completely encloses an entirety of the cap shielding element, the cap shell defining a hollow section of the cap, wherein the cap of the pig is removably attached to the base of the pig so that the cap shielding element and the base shielding element are in overlapping relationship with each other and do not contact one another, and so that an inner base shell portion of the base shell and an inner cap shell portion of the cap shell are in overlapping relationship with each other; and
   a syringe having a radiopharmaceutical therein enclosed within the pig, wherein at least a portion of a barrel of the syringe is located within the hollow section of the base of the pig, and wherein at least a portion of a plunger of the syringe is located within the hollow section of the cap of the pig.

2. The pig of claim 1, wherein the cap shielding element is made of lead.

3. The pig of claim 2, wherein the base shielding element is made of lead.

4. The pig of claim 1, wherein the base shielding element is made of lead.

5. The pig of claim 1, wherein the cap shell and the base shell comprise plastic material.

6. The pig of claim 1, wherein the cap shell and the base shell are made of plastic material.

7. The pig of claim 1, wherein the cap shell and the base shell comprise polycarbonate resin.

8. The pig of claim 1, wherein the cap shell and the base shell are made of polycarbonate resin.

9. The pig of claim 1, wherein the cap is elongate.

10. The pig of claim 1, further comprising a label attached to the syringe.

11. The pig of claim 1, further comprising a label attached to the base shell or the cap shell of the pig.

12. The pig of claim 1, wherein an exterior of at least one of the base shell and the cap shell comprises a plurality of flat surfaces.

13. The pig of claim 1, wherein the exterior of each of the base shell and the cap shell comprises a plurality of flat surfaces.

14. The pig of claim 1, wherein the syringe comprises finger grips that are disposed between a portion of the base shell and a portion of the cap shell.

15. The pig of claim 14, wherein the finger grips of the syringe are captured between the portion of the cap shell and the portion of the base shell.

16. The pig of claim 1, wherein the hollow section of the base is devoid of a removable inner liner.

17. The pig of claim 1, wherein the cap is removably attached to the base through complimentary threads located on the cap and the base.

18. The pig of claim 17, further comprising at least one locking detent associated with the threads.

19. The pig of claim 17, wherein the threads located on the cap and the base do not allow the cap to rotate more than three hundred and sixty degrees (360°) in relation to the base.

20. The pig of claim 17, wherein the threads located on the cap and the base do not allow the cap to rotate more than ninety degrees (90°) in relation to the base.

21. The pig of claim 1, further comprising a fluid-tight seal located between the cap and the base.

22. The pig of claim 1, wherein the polymer material of the base shell is molded about the base shielding element.

23. The pig of claim 1, wherein the polymer material of the cap shell is molded about the cap shielding element.

24. The pig of claim 1, further comprising a series of locking detents for securing the cap to the base.

25. The pig of claim 24, wherein the series of locking detents comprises four locking detents.

26. The pig of claim 25, wherein the cap is removably attached to the base through complimentary threads located on the cap and the base.

27. A radiopharmaceutical pig comprising:
an elongate base comprising:
a radiation-blocking base shielding element having an open end, a closed end, and at least one wall extending between the open and closed ends, the closed end and the at least one wall defining an interior of the base shielding element; and
a polymeric base shell that lines an entirety of the interior of the base shielding element, the base shell defining a hollow section of the base, and a cap removably attachable to the base, the cap comprising:
a radiation-blocking cap shielding element having an open end, a closed end, and at least one wall extending between the open and closed ends, the closed end and the at least one wall defining an interior of the cap shielding element; and
a polymeric cap shell that lines an entirety of the interior of the cap shielding element, the cap shell defining a hollow section of the cap; wherein the cap of the pig is removably attached to the base of the pig so that the cap shielding element and the base shielding element are in overlapping relationship with each other and do not contact each other, and so that an inner base shell portion of the base shell and an inner cap shell portion of the cap shell are in overlapping relationship with each other and
a syringe having a radiopharmaceutical therein, the syringe being disposed in the pig such that a portion of the syringe is captured between the cap shell and the base shell of the pig.

28. The pig of claim 27, wherein the syringe comprises a barrel, a plunger, and at least one finger grip extending outward from the barrel, the radiopharmaceutical being disposed within the barrel and the at least one finger grip of the syringe being captured between the cap shell and the base shell of the pig.

29. The pig of claim 28, wherein the barrel of the syringe is received in the hollow section of the base and the plunger of the syringe is received in the hollow section of the cap.

30. The pig of claim 27, wherein the cap shielding element comprises lead.

31. The pig of claim 27, wherein the base shielding element comprises lead.

32. The pig of claim 27, wherein the cap shell and the base shell comprise plastic material.

33. The pig of claim 27, wherein the cap shell and the base shell comprise polycarbonate resin.

34. The pig of claim 27, wherein the polymer material of the base shell is molded about the base shielding element.

35. The pig of claim 27, wherein the polymer material of the cap shell is molded about the cap shielding element.

36. The pig of claim 27, further comprising a series of locking detents for securing the cap to the base.

37. The pig of claim 36, wherein the series of locking detents comprises four locking detents.

38. The pig of claim 37, wherein the cap is removably attached to the base through complimentary threads located on the cap and the base.

39. The pig of claim 38, wherein the threads located on the cap and the base do not allow the cap to rotate more than three hundred and sixty degrees (360°) in relation to the base.

40. The pig of claim 38, wherein the threads located on the cap and the base do not allow the cap to rotate more than ninety degrees (90°) in relation to the base.

41. The pig of claim 27, further comprising a fluid-tight seal located between the cap and the base.

* * * * *